United States Patent [19]
Rock

[11] 4,359,463
[45] Nov. 16, 1982

[54] STABILIZATION OF FACTOR VIII ACTIVITY IN WHOLE BLOOD OR BLOOD PLASMA

[76] Inventor: Gail A. Rock, 270 Sandridge Rd., Rockclifee Park, Canada, K1L 5A2

[21] Appl. No.: 210,383

[22] Filed: Nov. 26, 1980

[51] Int. Cl.³ .............................................. A61K 35/14
[52] U.S. Cl. ............................... 424/101; 260/112 B; 260/112 R; 424/177
[58] Field of Search ............................. 424/101, 177; 260/112 B, 112 R

[56] References Cited

U.S. PATENT DOCUMENTS 4,203,891  5/1980  Rock ................................... 424/101

OTHER PUBLICATIONS

Weiss–Thrombosis et Diethesis Haemorrhagica, vol. 14, No. 32, (1965) pp. 32–51.
Pepper et al.–Transfusion, vol. 18, No. 6, (Nov.–Dec. 1978) pp. 756–760.
Article by Penick, et al., "Relative Stability of Plasma Antihemophilic Factor (AHF) under Different Conditions of Storage" appears at p. 1, line 18, et seq., of the Specification.
Article by Wolf–"Studies of Temperature and pH Stability of Human Antihaemophilic Factor (AHF) in Plasma and in Concentrate" is mentioned in the Spec. at p. 2, line 4, et seq.
Article by Preston–"The Factor–VIII Activity in Fresh and Stored Plasma" is mentioned in the Specification at p. 2, line 9, et seq.
Article by Vermeer, et al.,–"Contributions to the Optimal Use of Human Blood" is Mentioned in the Specification at p. 2, line 24, et seq.

Primary Examiner—Sam Rosen
Attorney, Agent, or Firm—Holman & Stern

[57] ABSTRACT

A method whereby initial Factor VIII activity normally present in blood collected into an anticoagulant which functions by chelating calcium is maintained for twenty-four or more hours without the necessity of the usual immediate freezing in either the whole blood or blood plasma. The method comprises mixing freshly collected blood or blood plasma prepared from that blood or freshly obtained blood plasma obtained by plasmapheresis, which blood or blood plasma has been collected into a calcium chelating anticoagulant, with a calcium-heparin solution in sufficient quantities to restore calcium to substantially normal physiological levels.

12 Claims, 1 Drawing Figure

STABILIZATION OF FACTOR VIII ACTIVITY IN WHOLE BLOOD OR BLOOD PLASMA

FIELD OF THE INVENTION

This invention relates to a method for maintaining Factor VIII activity, normally present in fresh blood at the time of collection. The Factor VIII activity is maintained either in the whole blood or in blood plasma prepared from it or in blood plasma obtained directly by plasmapheresis at levels equal to or close to the initial starting levels of Factor VIII for a period of twelve, twenty-four and even more hours.

Whole blood is generally collected for transfusion purposes into an anticoagulant which functions by chelating calcium and thus lowers the physiological level of calcium ions in the blood. In order to obtain a preparation enriched in Factor VIII activity, the whole blood is then separated into packed red cells (PC) and plasma. Following this and within six hours of collection, the plasma, containing the Factor VIII is frozen at very low temperature, preferably $-80°$ C., in order to maintain Factor VIII levels at reasonably high concentrations. The speed is necessary since it is well known that, if kept at room temperature, or indeed maintained under any condition other than the frozen state, the Factor VIII activity in whole blood or blood plasma produced from the whole blood rapidly decays.

DESCRIPTION OF THE PRIOR ART

Thus, for example Penick, G. C. and Brinkhous, K. M. reported in Relative Stability of Plasma Antihemophilic Factor (AHF) Under Different Conditions of Storage, (Am. J. Med. Sci. 232:434–442, 1956) that deterioration of AHF on storage tends to be slow but progressive, with about 30 to 60% of the initial AHF remaining after a 3-week storage period. These researchers studied several factors including the effects of initial plasma AHF level of the donor, care and collection of blood, various types of anticoagulants and the conditions of storage to determine the amount of AHF remaining in stored blood or plasma. It was found that the lower the temperature of storage, the better the preservation of Factor VIII, but that even did not prevent loss of half of the activity after one month.

Peter Wolf reported in Studies of Temperature and pH Stability of Human Antihemophilic Factor (AHF) in Plasma and in a Concentrate (Brit. J. Haemat. 5:169–176, 1959) that loss of AHF in trisodium citrate plasma stored at $+4°$ C. varied appreciably for different plasma samples, the losses obtained varied from 35 to 55% and 50 to 80% after storage times of 72 and 120 hours.

A. E. Preston reported in The Factor VIII Activity in Fresh and Stored Plasma, (Brit. J. Haemat. 13:42–59, 1967) that plasma Factor VIII is labile. Fresh blood stored at $4°$ C. lost its activity to a variable extent, reports on the exact loss differed considerably. By freezing the plasma at a temperature of a low of $-20°$ C. most of the Factor VIII activity could be preserved for long periods. This then provided a convenient method for a blood bank to keep stocks of plasma ready for emergency treatment of haemophilic patients. However, the process of freezing and later thawing plasma causes some loss of Factor VIII activity unrelated to the actual period of storage. Preston indicated that it was known that the Factor VIII activity of fresh plasma starts to decline between the 6th and 12th hour of storage and that freezing the plasma appeared to prevent further loss. The sooner plasma was frozen the better, since it took as much as six hours to be completely frozen to less than $-20°$ C. On these grounds it was thought prudent to start the cooling of the plasma as soon as possible. Centrifugation at $4°$ C. was recommended.

C. Vermeer et al. in Contributions to the Optimal Use of Human Blood: VIII. Stability of Blood Coagulation Factor VIII during Collection and Storage of Whole Blood and Plasma (Vox Sang. 31(Suppl. 1): 55–67, 1976) described a two phased decay curve for Factor VIII. The bi-phasic curve indicated that in fresh plasma, Factor VIII occurs in a stable and in a labile form. In cryoprecipitate from fresh plasma, these researchers detected the labile Factor VIII in a statistically significant amount. The amount of stable Factor VIII in fresh plasma could be found by extrapolation of the curve. These researchers indicated that 15 to 20 hours after the collection of blood, more than 50% of the initial Factor VIII can be obtained by cryoprecipitation, provided that the blood is stored between $10°$ and $20°$ C. and a pH of 6.9. This two phase decay curve was further described by M. D. Pepper et al in Plasma Factor VIII, Variables Affecting Stability under Standard Blood Bank Conditions and Correlation with Recovery in Concentrates (Transfusion 18(6):756–760, 1978). This study was designed to evaluate the loss of Factor VIII activity, especially within the first 18 to 24 hours of collection under normal blood bank conditions. In this study under the heading RESULTS, the authors reported the loss of Factor VIII activity in plasma stored at $4°$ C. in comparison with frozen plasma at $-40°$ C. Factor VIII decayed with a double half life, and the greatest loss occurred within the first 4 hours after collection. The main loss of Factor VIII and statistical significance during storage at $4°$ C. in the first 24 hours after collection were shown. The results of the study showed that Factor VIII decays at $4°$ C. in a bi-phasic manner. A rapid initial decrease with a half life of approximately 5 hours is followed by a relatively stable phase, with a half life of approximately 96 hours.

SUMMARY OF THE INVENTION

Thus, the present invention is concerned with a method whereby the initial Factor VIII activity normally present in blood collected into an anticoagulant which functions by chelating calcium is maintained for twenty-four or more hours without the necessity of the usual immediate freezing in either the whole blood or blood plasma.

In its broadest aspect, the present invention is directed to a method for maintaining Factor VIII activity in blood or blood plasma which comprises mixing freshly collected blood or blood plasma prepared from that blood or freshly obtained blood plasma obtained by plasmapheresis, which blood or blood plasma has been collected into a calcium chelating anticoagulant, with a calcium-heparin solution in sufficient quantities to restore calcium to substantially normal physiological levels.

Anticoagulants which function by chelating calcium are well known in the art. These anticoagulants function by combining with, precipitating and effectively removing calcium ions normally present in the blood. They therefore reduce the concentration of calcium ion in the blood below normal physiological levels. Generally, the anticoagulants which fall within this definition include the citrate anticoagulants, for example, acid citrate dextrose (ACD), citrate phosphate dextrose (CPD), and trisodium citrate (TSC). Ethylenediaminetetraacetic acid (EDTA) may also be used. CPD is the most preferred anticoagulant of the available citrates.

The heparin solution used in the method of the invention is preferably a sodium heparin preparation. It is preferably first mixed with the calcium and that solution-mixture is then mixed with the chelated blood or plasma. More preferably, the heparin solution is mixed so that it is present within the range of 4 to 8 units per ml.

The calcium added can be used in any soluble salt form, e.g. calcium chloride, and, as indicated, is added in quantities sufficient to restore levels of calcium to those near physiological levels. Preferably, the amount of salt added will be such that the calcium ion concentration is returned to approximately 5 mg %.

BRIEF DESCRIPTION OF THE DRAWINGS

In the drawings which are used to illustrate the present invention.

DESCRIPTION OF THE PREFERRED EMBODIMENTS

Figure 1:
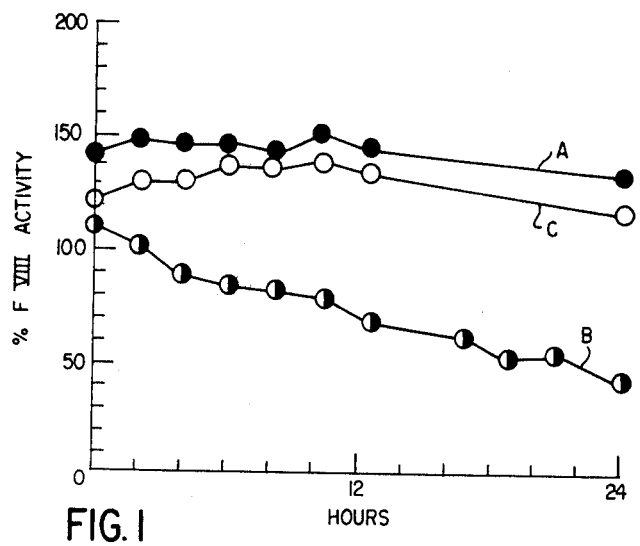
FIG. 1 is a graph showing decay curves for Factor VIII activity.

Referring first to FIG. 1, it will be seen that the graph includes 3 curves labelled A, B and C. Curve A is for plasma prepared from blood collected directly into heparin anticoagulant along. Curve B is for blood collected into citrate phosphate dextrose (CPD) and heparin anticoagulant, while curve C is for plasma prepared from blood collected into CPD to which the heparin-calcium mixture has been added immediately after collection of the blood (Heparin at 4–8 units/ml and sufficient calcium to give 5 mg % calcium ion concentration.)

The use of heparin alone as the anticoagulant provides a not unexpected result with respect to Factor VIII activity since it is not a chelating anticoagulant and as has been described earlier in U.S. Pat. No. 4,203,891, issued May 20, 1980 to G. A. Rock, collection of blood directly into heparin does provide substantially improved levels of Factor VIII activity. Curve B is of course the typical decay curve one would expect when a combination of heparin and CPD anticoagulants are employed. The chelating effect of the CPD anticoagulant and hence the lower level of calcium is evident. The use of heparin does not counter the effect of the low calcium level. However, the result shown by curve C is quite unexpected and indicates clearly that the best results can be obtained when the addition of the heparin-calcium mixture is made immediately following collection of blood.

Figure 3:
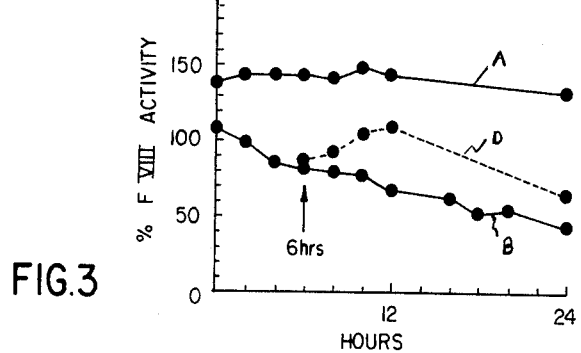
FIG. 3 shows decay curves for Factor VIII activity and illustrates the effect of delayed addition of the heparin calcium mixture of the invention.

It should be noted that in FIG. 3 the effects of the addition of the heparin-calcium mixture to blood up to six hours after collection is illustrated. Curves A and B are the curves shown in FIG. 1, while curve D is for plasma prepared by blood collected into CPD anticoagulant, treated with heparin and calcium six hours after the plasma was obtained (Heparin at 4–8 units/ml plasma and sufficient calcium to give 5 mg % calcium ion concentration). It can be seen that there is initially some improvement in the Factor VIII activity even when the heparin-calcium addition is made six hours after collection. However, the storage properties when the addition is made at this time are not as good as when the addition is made immediately after collection.

Figure 2:
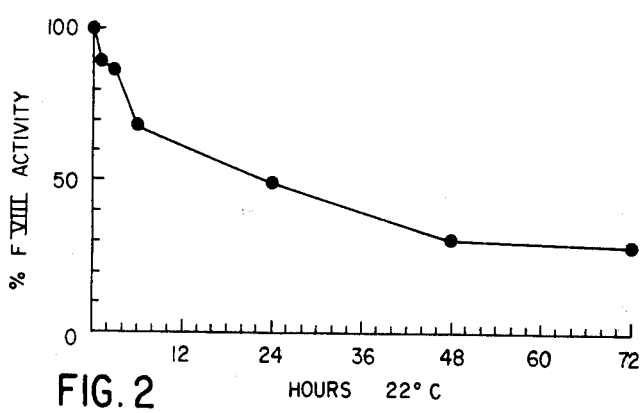
FIG. 2. is a typical two-phased decay curve showing Factor VIII activity in blood collected into CPD anticoagulant alone.

The two-phase decay curve found in FIG. 2 is the typical curve showing decay of Factor VIII activity in blood collected into CPD anticoagulant alone and as has been discussed earlier in the discussion of prior art.

The main advantage associated with the method of the present invention is that Factor VIII activity can be maintained at levels normally present at the time of blood collection for periods of time up to and in excess of twenty-four hours. This will provide adequate time after blood collection for transportation of blood from collection centres to a central or main processing centre without the necessity of other preserving methods. Thus, the method permits the maintenance of Factor VIII activity and hence Factor VIII production from whole blood or blood plasma at high levels without any complicated or unusual preserving methods being required. In addition to this advantage, this method permits the separation of CPD blood and plasma prior to the heparin-calcium treatment of plasma, thus eliminating the need to remove heparin if blood had been initially collected into CPD and heparin anticoagulant.

Following the addition of the heparin-calcium mixture, any of the well known commercial or laboratory procedures for producing Factor VIII from plasma can be applied to the resulting product. These include various salting out processes such as ethanol extraction of polyethylene glycol treatment of the plasma or cryoprecipitation and treatment of the resulting cryoprecipitate with any of the usual agents such as ammonium sulphate, ethanol, polyethylene glycol or any other compound or technique generally used to obtain a preparation enriched in Factor VIII. The advantage is of course that such processes need not take place immediately in order to obtain high yields of Factor VIII.

I claim:

1. A method for maintaining Factor VIII activity in blood or blood plasma comprising:
   collecting freshly obtained whole blood or blood plasma prepared from that blood or freshly obtained blood plasma prepared by plasmapheresis into a calcium chelating anticoagulant; and then
   mixing the collected product with a calcium-heparin solution, said calcium being added in sufficient quantity to restore calcium in said blood or blood plasma to substantially normal physiological levels.

2. A method as claimed in claim 1 wherein the heparin-calcium solution is added immediately following collection of the blood into the anticoagulant.

3. A method as claimed in claim 1 wherein the heparin-calcium solution is added immediately to the plasma obtained from the freshly collected blood.

4. A method as claimed in claim 1 wherein the heparin-calcium solution is added immediately to the plasma obtained by plasmapheresis.

5. A method as claimed in claim 1 wherein the heparin-calcium solution is added at a time not more than six hours subsequent to collection or obtaining the blood or plasma.

6. A method as claimed in any one of claims 2–5 or 1 wherein the anticoagulant is a citrate anticoagulant.

7. A method as claimed in claim 6 wherein the anticoagulant is citrate phosphate dextrose or acid citrate dextrose.

8. A method as claimed in any one of claims 2–5 or 1 wherein the blood or plasma is mixed with 4–8 units per ml of a heparin solution.

9. A method as claimed in claim 8 wherein the heparin solution is a sodium heparin solution.

10. A method as claimed in claim 1 wherein the calcium is added in any soluble salt form.

11. A method as claimed in claim 1 or 10 wherein the calcium is added in an amount sufficient to return the level of calcium in the blood to approximately 5 mg %.

12. A method as claimed in claim 7 wherein the blood or plasma is mixed with 4–8 units per ml of sodium heparin solution and the calcium is a soluble salt added in an amount sufficient to return the level of calcium in the blood to approximately 5 mg %.

* * * * *